United States Patent [19]

Wilmot

[11] Patent Number: 5,391,151
[45] Date of Patent: Feb. 21, 1995

[54] SUBCUTANEOUS INJECTOR

[75] Inventor: John G. Wilmot, Kent, England

[73] Assignee: Survival Technology, Inc., Rockville, Md.

[21] Appl. No.: 87,804

[22] PCT Filed: Jan. 14, 1992

[86] PCT No.: PCT/GB92/00081

§ 371 Date: Aug. 2, 1993

§ 102(e) Date: Aug. 2, 1993

[87] PCT Pub. No.: WO92/12745

PCT Pub. Date: Aug. 6, 1992

[30] Foreign Application Priority Data

Jan. 15, 1991 [GN] Guinea .................. 9100819

[51] Int. Cl.⁶ .............................................. A61M 5/20
[52] U.S. Cl. .................... 604/139; 604/135; 604/136
[58] Field of Search ............. 604/136, 135, 138, 139, 604/187, 134

[56] References Cited

U.S. PATENT DOCUMENTS

| 3,882,863 | 5/1975 | Sarnoff et al. | 604/136 |
|---|---|---|---|
| 4,178,928 | 12/1979 | Tischlinger | 604/139 |
| 4,227,528 | 10/1980 | Wardlaw | 604/139 |
| 4,258,713 | 3/1981 | Wardlaw | 604/139 |
| 4,553,962 | 11/1985 | Brunet | 604/198 |
| 4,983,164 | 1/1991 | Hook et al. | 604/139 |

FOREIGN PATENT DOCUMENTS

| 191508 | 8/1986 | European Pat. Off. . |
|---|---|---|
| 361668 | 4/1990 | European Pat. Off. . |
| 2638091 | 4/1990 | France . |

Primary Examiner—John G. Weiss
Attorney, Agent, or Firm—Cushman, Darby & Cushman

[57] ABSTRACT

A disposable, automatic, injector is disclosed which allows self-administration of a medicament to be injected subcutaneously. The injector comprises a barrel (1) with an inner chamber bounded by a liner (2). A first piston (4) and a second piston (11) are provided which may slide within the chamber with a fluid-tight seal with the liner (2). The second piston (11) carries an injection needle (13). A drive means, comprising a compression spring (5) and a releasable retaining collet (6), is provided to act on the first piston (4) to drive it towards the second piston (11). In operation, the drive means urges the first piston towards the second (11). The injection fluid, initially stored between the first and second pistons is incompressible and causes the second piston (11) to move until the needle (13) projects from the end of the barrel (1). When the needle (13) is fully extended the second piston (11) stops but the first piston (4) continues to move so causing injection fluid to be forced out through the needle (13).

22 Claims, 4 Drawing Sheets

SUBCUTANEOUS INJECTOR

This invention relates to a subcutaneous injector of the disposable automatic or 'one-shot' kind, that is to say, designed to discharge its contents into the user's body automatically and then to be thrown away. Such injectors are of great benefit in epidemics, and in third-world countries, and under battle conditions.

There have been many proposals for injectors involving a needle initially sealed within the body of the injector and acted on by a powerful spring released by an action on the part of the user, or by the act of placing the injector against the user's body (after release of a safety catch or pin), and the spring simultaneously acts on a piston to discharge the medicament or other contents through the needle.

Generally speaking these have involved a separate casing and spring mechanism into which is inserted a sealed ampoule or cartridge containing the medicament as well as the needle. After use the cartridge is thrown away and the injector is filled with a fresh cartridge, the spring being first re-compressed. Examples of such devices as shown in U.S. Pat. No. Nos. 2,832,339, 2,866,458 and 3,136,313. However fully disposable injectors or syringes are also known, i.e. ones in which the entire device is thrown away after use, and in these there is no separate cartridge. An example of a non-automatic injector of such a construction is shown in U.S. Pat. No. 4,059,109.

In the design of a disposable syringe or injector there are certain essential requirements, the most important being that of sterility and another important one is shelf life, i.e. a guarantee that there will be no corrosion, contamination, leakage or loss of sterility over a long period of storage. In the known disposable syringes and in the known disposable cartridges this is achieved by ensuring that the needle is in a wholly sterile environment, isolated from the atmosphere, right up to the moment of use. Generally speaking the needle is contained within a sheath and it penetrates the wall of this sheath as it advances under the force, direct or indirect, of the spring.

In some arrangements, e.g. that shown in U.S. Pat. No. 3,882,863, the needle is immersed in the medicament itself within the sheath, which in this case forms part of a cartridge. In others there is a piston carrying the needle, the medicament being behind the piston and the needle being in air, but still cut off from atmosphere.

In most of the known arrangements the injection of the medicament starts as soon as the needle penetrates the seal at the end of the sheath or the end of the barrel of the injector. Thus, from the moment the needle enters the user's body medicament is being dispensed. This is generally undesirable as what is really wanted is that the medicament should all, or substantially all, be placed below the skin.

The aim of the present invention is to overcome this problem and achieve a still further improvement in simplicity and reliability in a disposable syringe or injector.

According to the present invention there is provided a subcutaneous injector comprising;
a barrel having a chamber therein;
a first and second piston within the barrel each arranged to be slidable within the chamber the second piston carrying or being associated with an injection needle projecting away from the first piston;
a stop to restrain travel of the second piston towards an end of the barrel;
a releasable drive means; and
injection fluid substantially wholly contained in the portion of the chamber between the first and second pistons;

wherein upon its release the drive means urges the first piston towards the second piston so as to first cause the fluid contained therebetween to urge the second piston to move towards the end of the barrel, causing the injection needle to project therefrom, movement of the second piston eventually being restrained by the stop, further movement of the first piston then causing the injection fluid to be urged out through the injection needle.

According to another aspect of the invention we propose that a disposable subcutaneous injector comprises a first piston acted on by a spring held back until use by a safety catch, a second piston carrying the needle sealed to it, the medicament being contained substantially wholly in the space in the barrel defined between the two pistons, and -the needle projecting in air, not in medicament, from the second piston towards the end of the barrel where there are both a penetrable diaphragm seal and also a tubular seal or guide which is already entered by the tip of the needle in its rest position.

When the safety catch (which can be of a known kind, such as that shown in our own European Patent Specification No. 0 361 668) is released, the spring acts on the first piston to advance it and this in its turn, acting through the trapped virtually incompressible body of medicament, advances the second piston, pushing the needle through the seal and into the patient. Little or no medicament passes through the needle at this stage, but when the second piston reaches the end of its travel up against the end of the barrel, the first piston continues to advance under the action of the spring and dispenses the medicament into the patient through the needle.

It is a very important feature of the invention that during the initial advance of the needle the tubular seal through which the needle passes acts as a venting valve, opening away from the needle as the air in the progressively decreasing space between the second piston and the end of the barrel becomes compressed. In the absence of this venting seal that air would be trapped and would offer significant resistance to the advance of the second piston.

The action is at first sight similar to that of the injector disclosed in U.S. Pat. No. 3,882,863. However, it is important to note that in that known arrangement the medicament and the needle are contained in a separate disposable cartridge, the needle being immersed in the medicament, and as the whole cartridge advances under the action of the spring the air in the space between the front end of the cartridge and the end of the barrel can escape easily around the substantial clearance present between the outside of the cartridge and the inside of the barrel; the venting problem only arises in a disposable injector with an air-immersed needle.

One or more air escape channels may be provided from a region adjacent a seal in front of the needle to facilitate the escape of air. The body may have a front wall provided with an enlarged recess or aperture in the region where the needle is to pass through. The air escape channels may extend from the enlarged recess and may be formed in the internal walls of a separate end cap member attached to the body.

Alternatively or additionally air escape channels may be provided in a needle guide or a sealing bush surrounding the needle guide.

Embodiments of subcutaneous injectors according to the invention will now be described by way of example only with reference to the accompanying drawings of which:

Figure 1:
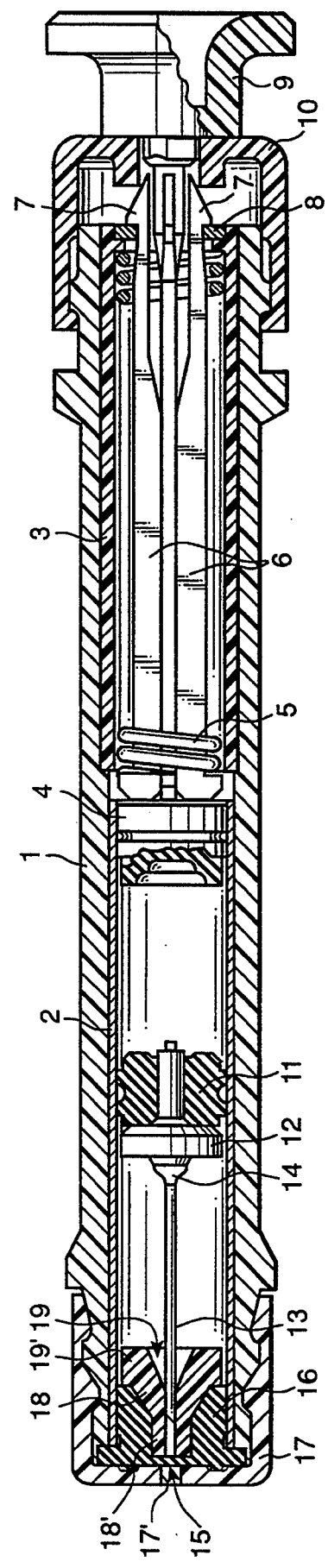
FIG. 1 is a longitudinal cross-section through a first automatic injector.

The injector of FIG. 1 comprises a body 1 injection-moulded polystyrene containing a barrel liner of F.E.P. 160 and a spring casing 3 of polystyrene. Sliding within the barrel liner 2 is a first piston or plunger 4 of rubber acted on by a stainless-steel coil compression spring 5. As used herein, the terms "piston" and "plunger" are interchangeable. In the initial condition of the injector the spring is held in the compressed position, as shown in the drawing, by a collet 6 made in two halves having at their tail ends detent teeth 7 engaging a latch ring 8 seated in the end of the spring casing 3. A safety pin 9 of moulded nylon normally keeps the teeth 7 apart but when it is withdrawn they can be urged together to release the collet 6 by a short movement of an end cap 10.

This spring-restraining and release mechanism is known and is substantially the same as that disclosed in our above-mentioned European specification.

Also within the barrel liner 2 and spaced about half way along in the initial condition is a second piston or plunger 11, also of rubber. Sealed into this piston is a moulded polyethylene needle-mounting 12 carrying the injection needle 13 sealed into it by adhesive 14.

In the condition shown, the tip of the needle 13 stops just short of a diaphragm seal 15 formed in a bush 16 which is held in the end of the barrel liner 2 by an end cap 17.

The tip of the needle 13 is received in a guide, or seal 18, of HD polyethylene shaped as shown, with its outside fitting into the bush 16 and its inside a good sliding fit on the needle. The guide seal 18 has a cylindrical portion 18' in which the tip of the needle 13 is slidingly and sealingly received, a tapered convergent conical portion 19 which helps to lead the needle into the bore of the guide during assembly of the injector, and an abutment rim flange 19' which abuts the rearmost end of the bush 16 and which serves as a stop for the piston 11 (as will be described later).

The space between the pistons contains the medicament and is in communication with the open rear end of the needle. The space between the second piston and the end of the body, i.e. the space around the needle, contains air or an inert gas.

When the injector is put to use by removing the safety pin 9 and actuating the end cap 10 to release the collet 6, the spring 5 initially advances both pistons together, as the liquid between them is virtually incompressible. The needle 13 advances through the guide 18 and penetrates the seal 15, emerging through the centre of a hole 17' in the end cap 17. The hole 17' is considerably larger in diameter than the needle 13 and the portions of the seal membrane 15 adjacent the hole pierced in it by the needle can open out into the larger hole 17'.

The air or gas in the space around the needle is able to force its way between the outside of the needle and the bore of the guide seal 18, and the membrane seal 15, and so does not hold up the advance of the second piston. This is an important feature and it means that the needle is able to advance fully into the patient's body until brought to halt when the mounting 12 comes up against the guide 18, and thereafter medicament is injected by the continued advance of the first piston. Only a negligible quantity, if indeed any at all, is injected during the advance of the needle.

The air between the guide seal 18 and the piston 11 may also be able to escape past the outer peripheral edges of the guide seal and the bush 16, and then past the snap fit of the end cap 17 and the forward end of the barrel 1.

There is thus provided a disposable injector which is simple to use, low in cost, contains few parts, and keeps the medicament itself and the needle in a wholly sterile condition up to the moment of use, and at the same time it ensures that during the use substantially the whole of the contents are injected subcutaneously, i.e. only when the needle has achieved the desired penetration.

Figure 2:
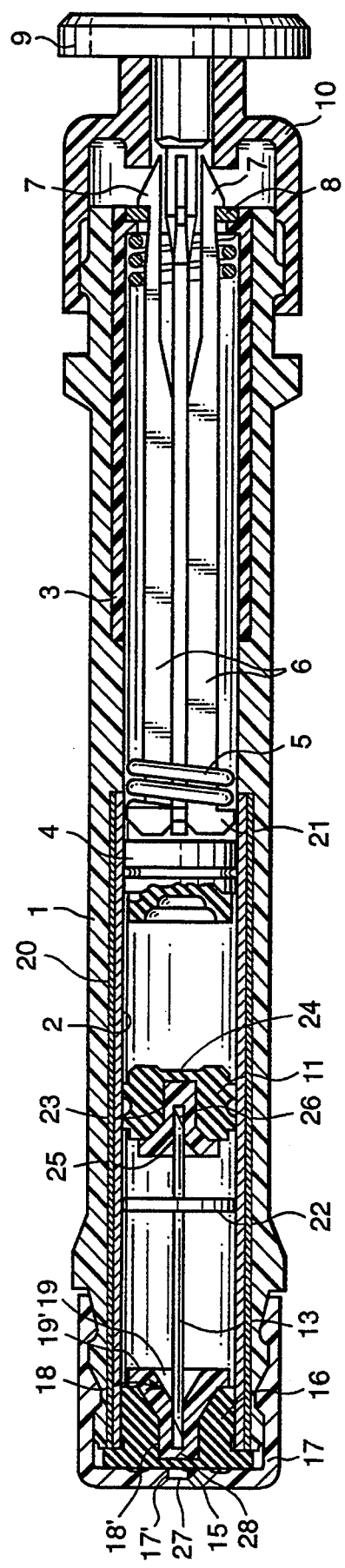
FIG. 2 is a longitudinal cross-section through a second automatic injector.

A second embodiment of the invention is shown in FIG. 2. The injector of FIG. 2 is in many ways very similar to that of FIG. 1 and similar components have been given the same reference numerals. The main differences are discussed below.

The liner 2 is made of glass, instead of plastics, and is shrink wrapped in a PVC sleeve 20. This makes the liner stronger, less fragile, and less likely to notch or scratch. Even if the glass sleeve should fracture the PVC sleeve maintains its structural integrity. The head of the collet 6 (referenced as No. 21) is received in the liner 2 prior to firing of the injector, and engages the inside walls of the liner 2. This ensures accurate alignment of the collet and liner during assembly of the injector and avoids any jarring impact on the liner should the collet hit the rearward end of the liner (which may sometimes occur in the embodiment of FIG. 1).

Impact between the collet and the liner is now impossible and this reduces the risk of the glass liner shattering during firing of the injector.

The second piston 11 and the mounting of the needle 13 relative to it are also different. The embodiment of FIG. 3 has a similar arrangement and shows the detail more clearly. The needle 13 is a double-ended needle having sharp points at each end and has a needle guide 22 such as a disc (perforated), cross, or the like swaged to it. The needle guide 22 mainly serves to transmit drive from the piston 11 to the needle 13, but also centres and guides the needle 13. The piston 11 has a stopped central bore 23 at its forward face and a membrane 24 at its rear face. A needle holder, or guide 25, is received in the bore 23 and holds the needle 13 and protects the membrane 24 from the needle. The holder 25 has an annular cylindrical portion closed by an end wall and a divergent tapered conical portion which facilitates the introduction of the needle 13 into the holder 25 during manufacture. The cylindrical portion of the holder 25 defines a central bore 26 in which the needle 13 is a tight sliding and sealing fit.

The end cap 17 has a membrane 27 closing the hole 17', and the guide seal 18 also has a membrane, membrane 28, closing its forward end. In some alternative embodiments the membranes 27 and/or 28 may be omitted.

When the injector is fired forward movement of the first plunger 4 is transferred to the second plunger 11 via the liquid medicament held between them and since the liquid is virtually incompressible serves as a hydraulic lock. The friction fit of the needle 13 in the holder 25 transfers the injection force from the holder to the needle. The needle 13 pierces the three membranes 28, 15, and 27 and continues to move forward until the needle guide 22 hits the abutment flange 19'. Further forward movement of the piston 11 moves the piston 11 relatively towards the needle guide 22 and the rear end of the needle pierces the end wall of the holder 25 and the membrane 24, communicating the needle with the medicament. Further forward movement of the piston 4 expells the medicament through the needle. It will be appreciated that the medicament does not contact the needle 13 until the injector is fired, and even then the medicament can be dispensed only after substantially all of the air in the injector forward of the piston 11 has been expelled out of the front of the injector. The bush 16 and guide valve 18 of the injector of FIG. 2 operate in the same way as those of FIG. 1.

It will also be appreciated that the cylindrical seal portion 18' of the guide 18 has a relatively tight sealing fit on the needle 13, but does not seal so tightly that air cannot be forced out of the injector between the cylindrical portion 18 and the needle during firing. In the embodiment of FIGS. 1 or 2 the cylindrical portion 18' may seal the unactuated injector against the ingress of atmospheric air past the needle, or it may not—the membrane 15 being sufficient.

The way of mounting the needle to the second plunger may be a separate invention.

Figure 3:
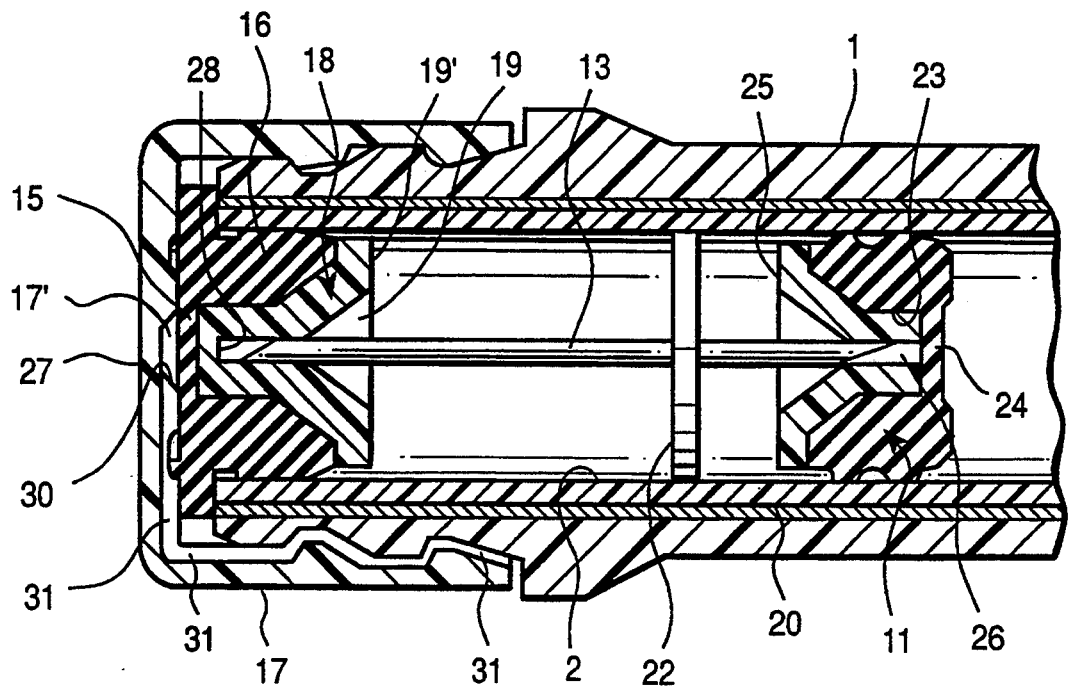
FIGS. 3 to 6 are longitudinal sections of the front ends of other, modified, injectors.

FIG. 3 shows the forward end of another automatic injector which is similar to that of FIG. 2 and the same reference numerals have been given to similar components.

The hole 17' in the end cap 17 is blocked by membrane 27, as in FIG. 2, but also has rounded or chamfered side walls 30 so as to define a wider recess adjacent the membrane seal 15. This allows the rubber membrane 15 to bellow into the recess and makes it easier to expel the gas from the needle chamber. This prevents the rubber needle guide from gripping to tightly on the needle tube as the tube passes through and creating too tight a seal. A groove 31 or series of grooves 31 are moulded into the end cap 17 to aid the gas to escape to atmosphere. The groove or grooves 31 extend from the recess along the front and side walls of the end cap 17 and to atmosphere.

Figure 4:
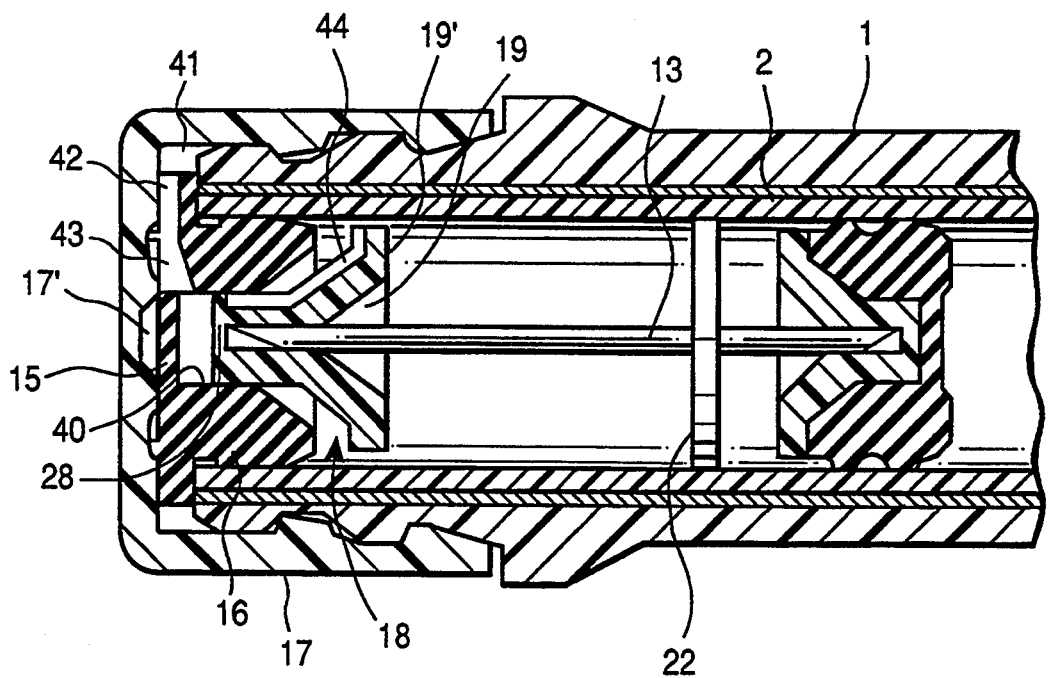

Another automatic injector is shown in FIG. 4 in which the needle guide 18 is movable relative to the bush 16 during the initial firing of the injector.

The bush 16 has a stopped internal bore 40 which communicates with an annular space 41 surrounding the forward end of the bush via a channel 42 in the bush. The channel 42 has an enlarged radially inner end 43. The annular space 41 communicates with atmosphere via the less than airtight attachment of the end cap 17 to the body 1. Air escape grooves, such as groove 31 of the embodiment of FIG. 3, may be provided to facilitate the escape of air.

The needle guide 18 is initially in the position shown in FIG. 4, with its forward membrane seal 28 spaced from the membrane 15 of the bush. The outer surface of the needle guide 18 has a communication groove 44 which is stopped just short of the forward end of the guide 18. It will be noted that the guide 18 is significantly smaller in diameter than the sleeve 2.

Prior to firing of the injector the parallel cylindrical sections of the needle guide 18 and bush 16 contact each other so as to form a sterile seal. When the injector is fired the friction of the needle in the needle guide 18 moves the needle guide 18 forward. As the needle pierces the membrane 28 and the membrane 15 the guide 18 is pushed fully into the bore 40. The groove 44 then communicates with end 43 of the channel 42 and air in the needle chamber has an easy escape route past the radially outer edges of the guide 18, through groove 44 and channel 42, and out between the end cap 17 and the body 1. Air can also leave the needle chamber between the needle guide and the needle, via hole or recess 17' (either directly out of the hole 17' after it has been formed by the needle, or out along the interface between the end cap and body).

Figure 5:
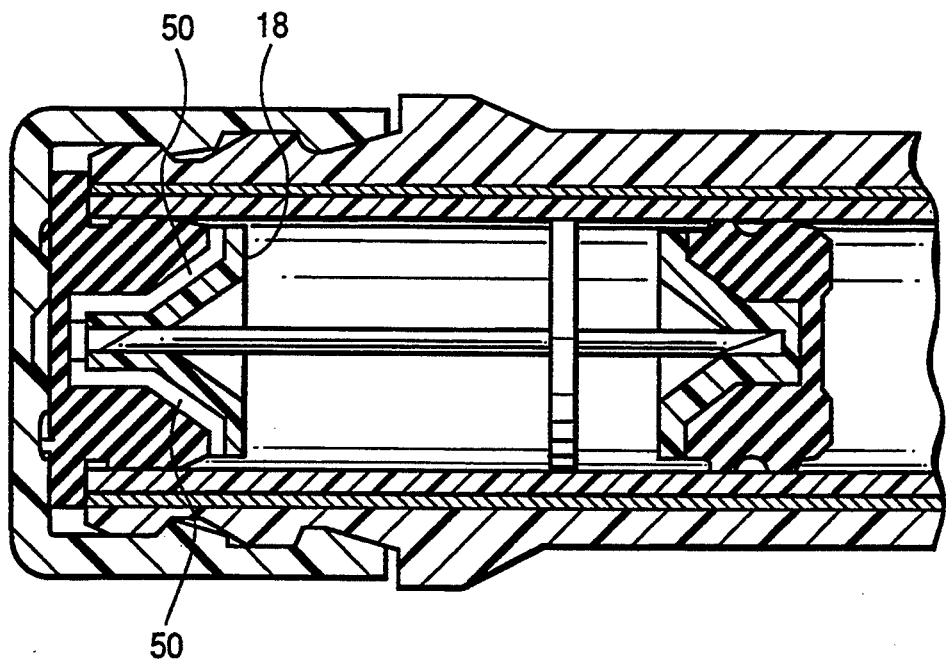

The embodiment of FIG. 5 is similar to that of FIG. 4, except that the needle guide 18 has a plurality of external grooves 50 and is fully introduced into the bush 16 during manufacture of the injector. The bush 16 may, or may not, have radial channels akin to channel 42, and the end cap may, or may not, have one or more air escape channels 31.

Instead or in addition to being grooved on its external surface the needle guide 18 may be grooved on its internal surface, adjacent the needle 13. Alternatively or additionally the bush 16 may have grooves on its internal surface.

Figure 6:
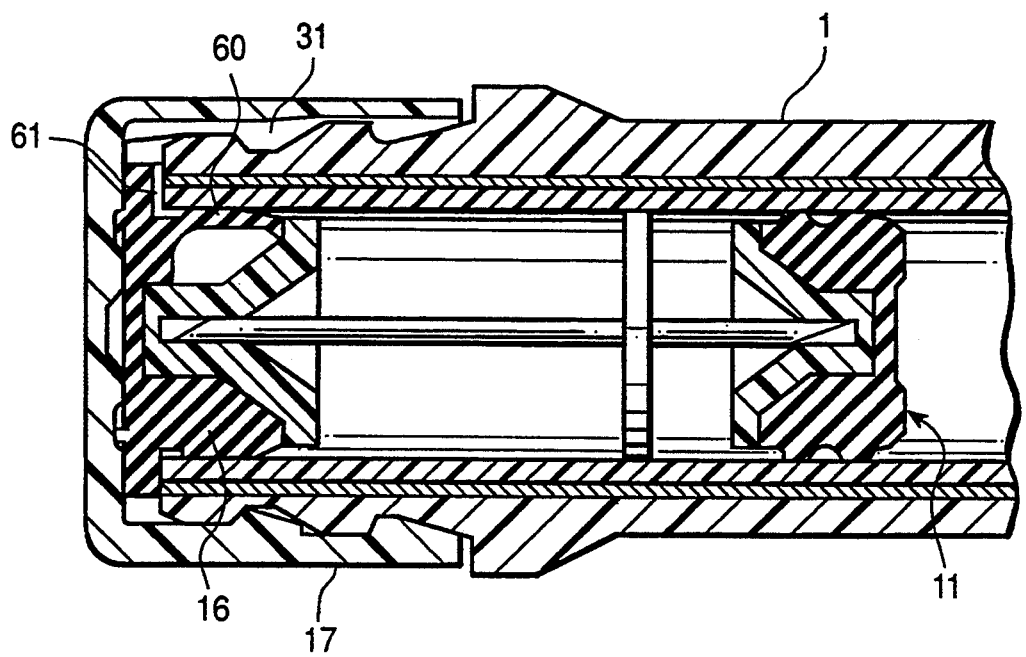

The automatic injector of FIG. 6 has a bush 16 which has a flexible, weakened, region 60 which in effect serves as a sealing lip. The bush 16 also has a radial passageway or groove 61 in the region of the weakened region 60. The wall of the bush 16 at the weakened region 60 is spaced slightly from the liner 2 at its rearmost end.

Prior to use the bush 16 seals around the liner 2 to form a sterile seal. Upon firing of the injector the increase of air pressure in the needle chamber distorts the bush at the weakened region 60, allowing the air to pass between the region 60 and the liner 2. The air enters air escape groove or grooves 31 in the end cap 17 via the groove 61.

A further modification which could be included in any of the embodiments described is that an air escape pathway may be provided in the front (external) face of the end cap 17. This prevents blockage of an air/gas path from the chamber surrounding the needle due to any potential sealing effect between the end cap and the patients' skin. The air escape pathway could comprise one or more grooves or channels, or a textured or roughened surface to the front face of the end cap.

I claim:
1. An automatic injector comprising:
   a body;
   a charge of medicament normally disposed within said body;
   a needle normally disposed in a normally sealed airspace within said body;
   a seal for sealing said air-space at a forward end of said body, said needle being drivable into a projecting position from the forward end of said body through a predetermined portion of said seal;
   a moveable plunger for forcing said medicament through said needle; and
   a releasable spring for driving said needle from said air-space into said projecting position from the forward end of said body and for moving said plunger to force said medicament through said needle, said injector having a normally sealed air release path associated therewith, said air release path being conditionable to permit at least some of the air normally contained in said air-space to exit said injector body before said needle is driven through said predetermined portion of said seal.

2. An automatic injector as claimed in claim 1, wherein said needle is driven into said projecting position from said body before said plunger is moved to force said medicament through said needle.

3. The injector according to claim 1, wherein said air release path permits air normally contained in said air-space to exit said injector body at a position which is spatially separated from said predetermined portion of said seal through which said needle is driven.

4. The injector according to claim 1, further comprising a barrel liner disposed in said body and a second plunger forwardly confining said medicament within said barrel liner in said body, said air release path being normally sealed by sealing contact between said seal and said barrel liner, said air release path being conditionable to permit said air normally contained within said air-space to exit said injector when said air normally contained within said air-space is compressed by movement of second movable plunger to force said seal and barrel liner to be moved out of said sealing contact therebetween.

5. An automatic injector comprising:
a body having a forward and rearward end;
a charge of medicament disposed within said body;
a needle having at least a portion thereof normally disposed in an air-space within said body, said needle having a longitudinal axis and being moveable along said axis to a fully projecting position in which a forward portion thereof projects from the forward end of said body, said needle being capable of dispensing said medicament when in said fully projecting position;
a moveable plunger capable of forcing said medicament through said needle to enable said needle to dispense said medicament; and
a releasable spring which, when released, operates to move said needle along said axis to said fully projecting position and to move said plunger so that said plunger forces said medicament through said needle when said needle is in said fully projecting position;
said injector being provided with an air release path through which air can escape from said air-space during an injection operation in which said releasable spring is released so that said needle moves along said axis to said fully projecting position, said air release path extending in a direction transverse to said longitudinal axis.

6. An automatic injection as claimed in claim 5, further comprising a forward piston forwardly confining said medicament, wherein a rearward end of said needle pierces said forward piston to expose a rearward opening of said needle to the medicament after said needle is moved to said fully projecting position.

7. An automatic injector as claimed in claim 5, wherein a seal member operates to forwardly confine said air contained within said air-space before said needle is moved to said fully projecting position, said seal member having an outer surface which defines at least part of said air release path.

8. An automatic injector as claimed in claim 7, wherein said seal member is covered by an end cap, said seal member and said end cap being punctured by said needle when said needle is moved along said longitudinal axis toward said fully projecting position.

9. An automatic injector as claimed in claim 8, wherein said air release path is provided, at least in part, between said seal member and said end cap.

10. An automatic injector comprising:
a body having a forward and rearward end;
forward and rearward pistons, said pistons being slidably moveable within said body;
a charge of medicament disposed between said forward and rearward pistons;
a needle having at least a portion thereof disposed in a sealed air-space within said body, said needle having a longitudinal axis and being moveable along said axis into a fully projecting position in which a forward portion of the needle projects from the forward end of said body, said needle having a rearward opening for receiving said medicament and a forward opening for dispensing said medicament; and
a releasable drive means for (1) driving said forward piston, said rearward piston and said medicament contained therebetween toward the forward end of the body, and (2) moving the needle along said longitudinal axis to said fully projecting position, said needle reaching said fully projecting position before said medicament is permitted to be dispensed from said forward opening of said needle;
said injector being provided with an air release path through which air contained within said air-space can be exhausted from said body as said needle is moved into said fully projecting position, said air release path extending in a transverse direction from said longitudinal axis of said needle.

11. An automatic injector as claimed in claim 10, wherein said needle is moved to said fully projecting position before said medicament is permitted to enter said rearward opening of said needle.

12. An automatic injector as claimed in claim 11, wherein a rearward end of said needle pierces said forward piston to expose said rearward opening of said needle to the medicament after said needle is moved to said fully projecting position.

13. An automatic injector as claimed in claim 10, wherein a seal member operates to forwardly confine said air contained within said air-space before said needle is moved into said fully projecting position, said seal member having an outer surface which defines at least part of said air release path.

14. An automatic injector as claimed in claim 13, wherein said seal member is covered by an end cap, said seal member and said end cap being punctured by said needle when said needle is moved along said longitudinal axis toward said fully projecting position.

15. An automatic injector as claimed in claim 14, wherein said air release path is provided, at least in part, between said seal member and said end cap.

16. An automatic injector as claimed in claim 10, wherein said releasable drive means comprises a spring.

17. An automatic injector as claimed in claim 10 wherein the needle passes through a guide seal which provides a sealingly sliding fit with said needle as said needle is driven into said projecting position.

18. An automatic injector as claimed in claim 17, wherein a forward tip of said needle is normally buried in said guide seal before it is driven into said projecting position.

19. An automatic injector comprising:
a body;
a barrel liner disposed within said body;
a charge of medicament normally disposed within said barrel liner;
a first plunger rearwardly confining said medicament within said barrel liner, said first plunger being movable within said barrel liner to dispense said medicament;
a second plunger forwardly confining said medicament within said barrel liner;
a seal disposed in normally sealing relation with said barrel liner at a forward portion thereof, said seal and said second plunger defining a normally sealed air space therebetween in said barrel liner;
a needle normally disposed in said sealed air-space within said barrel liner generally between said seal and said second plunger, said needle being drivable from said sealed air-space through a predetermined portion of said seal into a projecting position from the forward end of said body;
said seal being conditionable to permit at least a portion of the air normally sealed within said air space to escape therefrom at a position spaced from said predetermined portion of said seal through which said needle is driven; and
a releasable spring being releasable to i) drive said second movable plunger forwardly within said liner and thereby compress air normally disposed within said air space ii) drive said needle from said normally sealed air-space through said predetermined portion of the seal into said projecting position from the forward end of the body, iii) condition said seal to permit at least a portion of the air compressed in said air space to escape therefrom, and iv) move said first plunger within said barrel liner to dispense said medicament through said needle.

20. The injector according to claim 19, wherein said seal is conditioned to provide an air release path between said seal and said barrel liner, and wherein said air release path is normally sealed by sealing contact between said seal and said barrel liner, said air release path being conditionable to permit said air normally contained within said air-space to exit therefrom when said air normally contained within said air-space is compressed by movement of second movable plunger to force said seal and liner to be moved out of said sealing contact therebetween.

21. The injector according to claim 20, wherein said needle perforates said predetermined portion of seal to thereby provide an additional air release path between an exterior periphery of said needle and said seal to permit said air compressed within said air-space and normally disposed within said air-space to exit therefrom through said additional air release path.

22. The injector according to claim 19, wherein a rearward end of said needle perforates the second plunger so as to be in communication with the medicament after the needle is driven into said projecting position from the forward end of the body to thereby enable the needle to dispense the medicament therethrough.

* * * * *